(12) United States Patent
Azar

(10) Patent No.: US 7,015,039 B1
(45) Date of Patent: Mar. 21, 2006

(54) SEPARATING EPITHELIUM FROM STROMA IN LASEK SURGERY

(75) Inventor: Dimitri Azar, Brookline, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 434 days.

(21) Appl. No.: 10/214,676

(22) Filed: Aug. 8, 2002

(51) Int. Cl.
*C12N 5/00* (2006.01)

(52) U.S. Cl. .............. 435/404; 424/724; 435/366; 435/371; 435/1.1; 606/5

(58) Field of Classification Search .......... 435/404, 435/366, 371, 1.1; 606/5; 424/724
See application file for complete search history.

(56) References Cited

U.S. PATENT DOCUMENTS

| | | | | |
|---|---|---|---|---|
| 4,427,774 A | * | 1/1984 | Yukawa et al. | 435/115 |
| 4,443,544 A | * | 4/1984 | Rogers et al. | 435/162 |
| 5,630,810 A | * | 5/1997 | Machat | 606/5 |
| 6,335,006 B1 | * | 1/2002 | Miller | 424/78.04 |

OTHER PUBLICATIONS

Chen et al., "Human Corneal Epithelial Cell Viability and Morphology after Dilute Alcohol Exposure", vol. 43, No. 8 *IOVS* (2002), pp. 2593-2602.

* cited by examiner

*Primary Examiner*—Leon B. Lankford, Jr.
(74) *Attorney, Agent, or Firm*—Fish & Richardson P.C.

(57) ABSTRACT

A method of separating the epithelium and the stroma of a cornea includes providing a solution that includes a detaching agent diluted in a culture medium and applying the solution to the surface of the cornea.

2 Claims, No Drawings

SEPARATING EPITHELIUM FROM STROMA IN LASEK SURGERY

FIELD OF INVENTION

This invention relates to ophthalmic surgery, and in particular, to surgery on the cornea.

BACKGROUND

The cornea of the eye plays a role in focusing light. By changing the shape of the cornea, it is possible to correct a patient's vision. Common surgical procedures for changing the shape of the cornea include temporarily removing the epithelium of the cornea to expose the underlying stroma, ablating selected portions of the stroma with a laser, and replacing the epithelium over the stroma. Two known surgical methods are LASEK ("Laser assisted Sub Epithelial Keratomilieusis") and LASIK ("Laser assisted In situ Keratomilieusis") surgery.

In LASEK surgery, an incision along a circular arc on the cornea is made and the resulting flap is pulled back to expose the stroma of the cornea. The flap includes the epithelium and the Bowman's membrane separating the epithelium from the stroma. Unlike the flap that is made during LASIK, this flap does not include any portion of the stroma. Thus, when the flap is pulled back, it is the surface of the stroma, and not the interior of the stroma, that is exposed to the laser. This procedure thus results in a lower risk of complications.

In practice, because the epithelium is so thin, it is difficult to cut a flap without cutting into the stroma. It is known, however, that bathing the cornea in a solution of alcohol and water causes separation of epithelial cells from the stroma. Once the epithelium is separated from the stroma, cutting the flap becomes easier.

A difficulty with the use of the foregoing solution is that alcohol is toxic to cells. Thus, if the concentration of alcohol is excessive, or if the solution is left on the cornea for too long, a significant number of epithelial cells will die. If this occurs, the flap will not re-attach itself effectively to the stroma.

SUMMARY

The invention is based on the recognition that diluting a detaching agent with a culture medium results in a solution having reduced cytotoxicity.

One aspect of the invention is a method of separating the epithelium and the stroma of a cornea by providing a solution that includes a detaching agent diluted in a culture medium. This solution is then applied to the surface of the cornea.

Another aspect of the invention is a solution for detaching the stroma and the epithelium of a cornea. Such a solution includes a detaching agent and a diluent that includes a culture medium.

In some embodiments, the culture medium includes a cell, or tissue culture medium. Other embodiments are those in which the culture medium is a corneal transplant medium.

The detaching agent can include an alcohol, such as ethanol. In some embodiments, the alcohol is diluted to be in a concentration that ranges from approximately 10% to approximately 20%. In other embodiments, the concentration of alcohol is selected to be sufficient to detach the epithelium from the stroma.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

A surgical method according to the invention includes application of a solution containing ethanol and a cell culture medium. It has been found in animal studies that when bathed in such a solution for approximately thirty seconds, the epithelium begins to detach from the stroma. The substitution of cell-culture medium for water as a diluent for the ethanol reduces cell death in the epithelium without significantly compromising the ethanol's ability to detach the epithelium.

A suitable cell culture medium is a corneal transport solution that is used to bathe corneas intended for transplant. Examples of such corneal transport solutions include those sold under the marks K-SOL and MK MEDIUM.

The concentration of ethanol in the cell culture medium is approximately 20%. However, the exact concentration used in a particular application can vary depending on the instrument used to form the flap and in the specific properties of the patient's cornea.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

I claim:

1. A method of separating the epithelium and the stroma of a cornea, the method comprising:
   providing a solution that includes a detaching agent diluted in a cell culture medium to a concentration sufficient to detach the epithelium from the stroma; and
   applying the solution to the surface of the cornea.

2. The method of claim 1, further comprising diluting the ethanol to a concentration in a range between approximately 10% and approximately 20%.

* * * * *

UNITED STATES PATENT AND TRADEMARK OFFICE
CERTIFICATE OF CORRECTION

| | |
|---|---|
| PATENT NO. | : 7,015,039 B1 |
| APPLICATION NO. | : 10/214676 |
| DATED | : March 21, 2006 |
| INVENTOR(S) | : Dimitri T. Azar |

Page 1 of 1

It is certified that error appears in the above-identified patent and that said Letters Patent is hereby corrected as shown below:

Col. 2, line 52;

In claim 1, line 3, delete "a detaching agent" and insert --ethanol-- in its place.

After claim 2, insert the following:

Col. 2, line 59;

--3. The method of claim 1, further comprising selecting the culture medium to be a corneal transport medium.--

Signed and Sealed this

First Day of July, 2008

JON W. DUDAS
*Director of the United States Patent and Trademark Office*